US011124629B2

(12) United States Patent
Roggenstein et al.

(10) Patent No.: US 11,124,629 B2
(45) Date of Patent: Sep. 21, 2021

(54) REGENERATED CELLULOSE FIBER

(71) Applicant: KELHEIM FIBRES GMBH, Kelheim (DE)

(72) Inventors: Walter Roggenstein, Bad Abbach (DE); Frank Hermanutz, Leonberg (DE); Philipp Wimmer, Regensburg (DE)

(73) Assignee: KELHEIM FIBRES GMBH, Kelheim (DE)

( * ) Notice: Subject to any disclaimer, the term of this patent is extended or adjusted under 35 U.S.C. 154(b) by 0 days.

(21) Appl. No.: 14/651,341

(22) PCT Filed: Dec. 4, 2013

(86) PCT No.: PCT/EP2013/075580
§ 371 (c)(1),
(2) Date: Jun. 11, 2015

(87) PCT Pub. No.: WO2014/090665
PCT Pub. Date: Jun. 19, 2014

(65) Prior Publication Data
US 2015/0329707 A1 Nov. 19, 2015

(30) Foreign Application Priority Data
Dec. 13, 2012 (EP) .................... 12197065

(51) Int. Cl.
*C08L 1/02* (2006.01)
*D21H 13/08* (2006.01)
*D04H 3/013* (2012.01)
*A61L 26/00* (2006.01)
*A24D 3/10* (2006.01)
*D01F 2/10* (2006.01)

(52) U.S. Cl.
CPC .............. *C08L 1/02* (2013.01); *A24D 3/10* (2013.01); *A61L 26/0095* (2013.01); *D01F 2/10* (2013.01); *D04H 3/013* (2013.01); *D21H 13/08* (2013.01); *Y10T 428/249921* (2015.04); *Y10T 442/60* (2015.04)

(58) Field of Classification Search
CPC ......... C08L 1/02; A24D 3/10; A61L 26/0095; D04H 3/013; D10B 2201/20–28; D10B 2401/021
USPC ....................................................... 428/393
See application file for complete search history.

(56) References Cited

U.S. PATENT DOCUMENTS

| | | | |
|---|---|---|---|
| 2,231,890 A | 2/1941 | Esselmann et al. | |
| 2,234,734 A | 3/1941 | Kline | |
| 2,902,391 A | 9/1959 | Daul et al. | |
| 2,903,382 A | 9/1959 | Berls | |
| 3,232,823 A | 2/1966 | Soblev | |
| 3,347,968 A | 10/1967 | Rainer et al. | |
| 3,408,291 A | 10/1968 | Thomas et al. | |
| 3,418,405 A * | 12/1968 | Kajitani | D21H 13/08 264/190 |
| 4,352,770 A * | 10/1982 | Turbak | D01F 2/02 264/187 |
| 4,770,925 A | 9/1988 | Uchikawa et al. | |
| 5,008,385 A * | 4/1991 | Diamantoglou | B01D 71/12 264/187 |
| 5,163,931 A | 11/1992 | Aldrett | |
| 5,935,844 A * | 8/1999 | Matsumura | C02F 3/085 435/262.5 |
| 5,968,855 A | 10/1999 | Perdelwitz, Jr. et al. | |
| 6,342,268 B1 | 1/2002 | Samain | |
| 6,372,035 B1 | 4/2002 | Juppo et al. | |
| 2003/0092804 A1 | 5/2003 | Detering et al. | |
| 2004/0259445 A1 | 12/2004 | Hilfenhaus et al. | |
| 2005/0176326 A1 | 8/2005 | Bond et al. | |
| 2005/0245159 A1 | 11/2005 | Chimielewski et al. | |
| 2006/0060814 A1 | 3/2006 | Pawlowska et al. | |
| 2007/0026228 A1 * | 2/2007 | Hartmann | D01F 1/08 428/402.2 |
| 2007/0118087 A1 | 5/2007 | Flohr et al. | |
| 2007/0219517 A1 | 9/2007 | Rosenfeld et al. | |
| 2008/0146792 A1 * | 6/2008 | Wang | C08B 31/04 536/107 |
| 2009/0131909 A1 | 5/2009 | Bjornberg et al. | |
| 2011/0021098 A1 | 1/2011 | Tabellion et al. | |
| 2011/0045078 A1 | 2/2011 | Kolbe et al. | |
| 2013/0236647 A1 | 9/2013 | Samain et al. | |

(Continued)

FOREIGN PATENT DOCUMENTS

| | | |
|---|---|---|
| CH | 213876 A | 3/1941 |
| CH | 359832 A | 1/1962 |
| DE | 1222204 B | 8/1966 |

(Continued)

OTHER PUBLICATIONS

JP2010106251A English Machine Translation, from ip.com, translated Dec. 1, 2017.*
Incorporated, Define Incorporated at Dictionary.com, http://www.dictionary.com/browse/incorporated, retreived Feb. 14, 2017.*
Disintegrate, Definition of, Merriam-Webster, https://www.merriam-webster.com/dictionary/disintegrate, retreived Aug. 27, 2020.*
Deanin, Rudolph D., et al. "Breathable, Permanent Water-Repellent Treatment of Cotton 1", textile Research Journal, Nov. 1970, vol. 40, No. 11, pp. 970-974.

(Continued)

*Primary Examiner* — Jennifer A Gillett
(74) *Attorney, Agent, or Firm* — Venable LLP

(57) ABSTRACT

The present invention relates to a regenerated cellulose fiber which contains a hydrophobic substance selected from the group consisting of alkyl ketene dimers, alkenyl ketene dimers, alkyl succinic anhydrides, alkenyl succinic anhydrides, alkyl glutaric acid anhydrides, alkenyl glutaric acid anhydrides, alkyl isocyanates, alkenyl isocyanates, fatty acid anhydrides as well as mixtures thereof incorporated in the cellulose matrix.

8 Claims, No Drawings

(56) References Cited

U.S. PATENT DOCUMENTS

| | | |
|---|---|---|
| 2014/0315461 A1 | 10/2014 | Schachtner et al. |
| 2015/0329707 A1 | 11/2015 | Roggenstein et al. |

FOREIGN PATENT DOCUMENTS

| | | | |
|---|---|---|---|
| DE | 1468539 | A1 | 12/1968 |
| DE | 1469448 | A1 | 3/1969 |
| DE | 3317724 | A1 | 11/1983 |
| DE | 3920356 | A1 | 12/1989 |
| DE | 69801056 | T2 | 11/2002 |
| DE | 102006053326 | A1 | 5/2008 |
| DE | 10200754702 | A1 | 5/2009 |
| EP | 0228576 | A1 | 7/1987 |
| EP | 0353212 | A1 | 1/1990 |
| EP | 0947549 | A1 | 10/1999 |
| FR | 707688 | A | 7/1931 |
| FR | 2767270 | A1 | 2/1999 |
| GB | 343104 | | 2/1931 |
| GB | 477029 | A | 12/1937 |
| GB | 586549 | A | 3/1947 |
| GB | 780967 | A | 8/1957 |
| GB | 887466 | A | 1/1962 |
| GB | 1042182 | A | 9/1966 |
| GB | 2121069 | A | 12/1983 |
| GB | 2126260 | A | 3/1984 |
| GB | 2221928 | A | 2/1990 |
| GB | 2252984 | A | 8/1992 |
| JP | 2006307402 | A | 11/2006 |
| JP | 2010106251 | A * | 5/2010 |
| WO | 9908724 | A2 | 2/1999 |
| WO | 9937859 | A1 | 7/1999 |
| WO | 0163036 | A1 | 8/2001 |
| WO | 2004/024044 | A1 | 3/2004 |
| WO | 2012066015 | A1 | 5/2012 |
| WO | 2013/067556 | A1 | 5/2013 |
| WO | WO-2013067556 | A1 * | 5/2013 ............ D06M 13/13 |

OTHER PUBLICATIONS

Notification of Transmittal of Translation of the International Preliminary Report on Patentability and Written Opinion issued in International Application No. PCT/EP2013/075580 dated Jun. 26, 2015—6 pages.

R. Adams, "Organic Reactions vol. III," John Wiley & Sons Inc. NY, p. 146 (1946).

J.C. Sauer, "Ketene Dimers from Acid Halides," Journal of the American Chemical Society, vol. 69, pp. 2444-2448 (1947).

H. Zhang, "The Role of Vapour Deposition in the Hydrophobization Treatment of Cellulose Fibres using Alkyl Ketene Dimers and Alkenyl Succinc Acid Anhydrides," Colloids and Surfaces A: Physiochem. Eng. Aspects, vol. 297, pp. 203-210 (2007).

Collier, B. J., et al. "Understanding Textiles" Prentice-Hall, 6th Ed., p. 492 (2001).

Incorporated, Define Incorporated at Dictionary.com, available at http://www.dictionary.com/browse/incorporated, retrieved Feb. 14, 2017.

K. Brederck and F. Hermanutz, "Man-made cellulosics," Rev. Prog. Color, 35, pp. 59-75 (2005).

* cited by examiner

REGENERATED CELLULOSE FIBER

BACKGROUND OF THE INVENTION

Field of the Invention

The present invention relates to a regenerated cellulose fiber, in particular a regenerated cellulose fiber obtained according to the viscose process.

Description of Related Art

In particular, the present invention deals with a regenerated cellulose fiber having hydrophobic properties.

The use of alkyl ketene dimers (AKD) and further fatty acid derivatives as a sizing agent for the water repellent finishing of paper is known (e.g., DE 3 920 356). In doing so, the cellulose in the paper is rendered water repellent by the fatty acid residue of the reactants, which is attached via an ester bond. Areas of application are, for example, writing papers, photo papers and food wrappings.

Likewise, the influencing of the percentage of water absorption of viscose fibers by incorporating hydrophilic and/or hydrophobic auxiliary materials has been known for quite a while. The auxiliary materials contribute to the total mass of the fibers, but do not absorb any water themselves. Examples are: barium sulfate, heavy metal sulfides, carbon, polyolefins (DE 1 469 448 A1, DE 3 317 724 A1, U.S. Pat. No. 2,234,734 A).

In case of such an introduction of filler materials, as a rule, merely a mass effect is generated, as a result of the filler share being factored into the total mass. In doing so, the total water absorption of the fiber is indeed reduced, since the filler materials themselves do not absorb any water, in most cases, however, no hydrophobic effect is achieved. In addition, the filling of the fiber leads to a substantial loss in fiber strength.

In addition, DE 3 317 724 A1 mentions the incorporation of hydrophobic, oligomeric or polymeric substances, wherein inert polymers such as polyethylene, polypropylene, PTFE etc. are specifically mentioned.

Also known is an aftertreatment of fibers with nanoparticles using binders (DE 10 2006 053326 A1), by grafting hydrophobic substances onto cellulose (e.g., methyl methacrylate: DE 1 468 539 A), by creating water repellency through a reaction of cellulosic textile fibers with polyiso- or polyisothiocyanate, respectively, (GB 586549A), by a reactive aftertreatment of fibrous materials/textiles, e.g., etherification via acetal binding (GB 477 029A), esterification with acid chlorides in organic solvents such as pyridine and DMF (FR 707 688A and, respectively, Textile Research Journal, 40 (1970), 970 et seqq.).

It has also been described to introduce fatty acid chlorides in an inert solvent and to carry along and discharge unreacted reactants as well as hydrogen chloride as a reaction product in the hot gas stream (DE 69801056T2, WO 2012/066015 A, FR 2 767 270 A1).

The alcoholate-induced esterification of fibers with fatty acid salts (GB 780967A) has been described just as the textile aftertreatment with AKD dispersions (GB 2 221 928A).

On the one hand, those previously known aftertreatments are performed as a coating, i.e., merely on the surface of the fiber or of the textile article, respectively. On the other hand, they can be performed reactively, wherein, however, in that case too, the reaction takes place only in areas of the fiber close to the surface, since the reactants are not able to penetrate unhindered into the interior of the fiber. Moreover, the consumption of water repellent finishing agents is high, since, for example in case of an aftertreatment with AKD, the latter reacts already in the heat with the water present at a significant surplus and, thus, is not available anymore for a reaction with the cellulose.

Via the aftertreatment, a water-repellent surface is formed, after the destruction of which, however, the fiber absorbs water unhindered and irreversibly.

The gas-phase supported water repellent finishing of surfaces has been demonstrated by means of paper samples, wherein, however, distinct differences were visible between the two sides of the paper. The hydrophobic effect could be eliminated largely by extraction with acetone, which was indicative of a high share of hydrolysis during the reaction of the fatty acid chlorides with the cellulose. In that case too, the fatty acid chlorides in the gas phase cannot diffuse freely into the interior of the fiber, but primarily attach themselves on the outside.

Furthermore, the so-called "animalizing" of spinnable fibers by spinning in a polymerization product of aromatic iso- or isothiocyanate, respectively, and cyclic imine or a polymer of the latter, respectively, is known (CH 213876). A partial creation of water repellency was observed in the process, that, however, only in case of very high additivations with a water-repellent polymeric agent, the distribution of which was enough for sufficiently reducing the surface energy of the fiber. In addition, the fibers thus obtained rather have the nature of wool fibers due to the high additive content.

In order to improve the demoldability of sausage from viscose sausage casings, those were aftertreated with AKD in an aqueous suspension, or else the viscose mass was mixed with an AKD suspension or emulsion before the casing was formed (GB 887 466A, GB 1 042 182 A). In those documents, a water-repellent effect is not described, merely the casing's higher affinity for fats is mentioned. The fundamental difference between viscose fibers and sausage casings consists in that, as a rule, the sausage casings consist of papers soaked with a viscose mass and, in rare cases, of pure viscose. In the latter case, the viscose is not provided in the form of a fiber, but as a thick tube with wall thicknesses of approx. 50 μm and more.

The present invention has as its object to provide a regenerated cellulose fiber obtained in particular according to the viscose process and having hydrophobic properties, which does not exhibit the above-described disadvantages of the recommendations of the prior art. In addition, the fiber should be biodegradable.

Said object is achieved with a regenerated cellulose fiber which contains a hydrophobic substance selected from the group consisting of alkyl ketene dimers, alkenyl ketene dimers, alkyl succinic anhydrides, alkenyl succinic anhydrides, alkyl glutaric acid anhydrides, alkenyl glutaric acid anhydrides, alkyl isocyanates, alkenyl isocyanates, fatty acid anhydrides as well as mixtures thereof incorporated in the cellulose matrix.

Surprisingly, it has been found that the incorporation of reactive hydrophobic substances such as AKD into the cellulose matrix of a regenerated cellulose fiber can be performed successfully. In this way, a water-repellency producing effect distributed across the entire fiber cross-section is achieved, which is "permanent", i.e., which is not eliminated by a surface treatment of the fibers such as, e.g., wash steps or other treatments.

Furthermore, it has been found that, by incorporating reactive hydrophobic substances into the cellulose matrix, the fundamental properties of the visose fibers, e.g., the possibility of absorbing water vapour, are not impaired.

For their incorporation, the hydrophobic substances must be added to the spinning viscose or to a precursor thereof. In doing so, it is surprising that substances such as AKD have turned out to be stable in the viscose spinning process, since AKD, for example, disintegrates quickly in an alkaline environment.

In the cellulose fiber according to the invention, the content of the hydrophobic substance in the fiber preferably ranges from 0.1% by weight to 13% by weight, particularly preferably from 1% by weight to 7.5% by weight, based on cellulose.

The titer of the fiber according to the invention may range from 0.5 to 40 dtex, in particular from 2 to 28 dtex.

The fiber according to the invention may be provided as a short cut fiber having a length of cut of from 2 to 20 mm, particularly preferably of from 3 to 12 mm. In particular for the application in nonwoven fabrics and textiles, the fiber may also be provided as a staple fiber with a length of cut of from 20 mm to 150 mm, in particular of 40 to 110 mm, particularly preferably of 40 mm (cotton type) and 70 mm (wool type).

The process for the production of a cellulose fiber according to the invention comprises the step of adding the hydrophobic substance to a spinning viscose or a precursor thereof.

A person skilled in the art understands a "spinning viscose" to be an aqueous alkaline solution of cellulose xanthogenate. Starting materials and intermediate products of the viscose process, for example, the pulp used, the pulp after alkalization, or also the dissolving lye used for dissolving the cellulose xanthogenate, are understood to be "precursors" of a spinning viscose.

The present invention also relates to the use of the cellulose fiber according to the invention in sanitary products, in particular in cover sheets/back sheets, in cosmetic and baby wipes, in medical products, in particular in wound dressings, in papers and wet-laid nonwovens, in textile applications, in particular sportswear and protective clothing and/or in nonwoven fabrics and filter media, in particular cigarette filters.

EXAMPLES

Hydrophobic substances of the following substance classes were added to a spinning viscose:

a) a vinyl acetate copolymer (Vinnapas EN 1028, manufacturer: company Wacker)

b) a quaternary fatty acid derivative (Adulcinol BUN, manufacturer: company Zschimmer & Schwarz)

c) an alkyl ketene dimer (AKD) (Ukasol NL-201, manufacturer: company Schill & Seilacher)

d) a further quaternary fatty acid derivative (Stantex s6557, manufacturer: company Pulcra Chemicals)

e) a fatty alcohol combination (Setilon KN, manufacturer: company Pulcra Chemicals)

f) a fatty acid condensation product (Duron OS 2160, manufacturer: company CHT) and g) ester oils (Duron OS 3136, manufacturer: company CHT)

It has been attempted to spin viscose fibers from the thus modified spinning viscoses in the usual manner. Only in cases c) and g) it has been possible to successfully spin out fibers.

An increase in the hydrophobicity of the produced fibers (examined on the basis of the sinking of the fibers into water) could be observed only in case c) (water repellent finishing with AKD).

What is claimed is:

1. A regenerated viscose fiber having a cellulose matrix, wherein said fiber is produced according to a viscose process, wherein said fiber is water-repellant and comprises a hydrophobic substance incorporated into the cellulose matrix by adding the hydrophobic substance into a spinning solution or a precursor thereof during the viscose process, wherein the hydrophobic substance is an alkyl ketene dimer wherein the content of the hydrophobic substance in the regenerated viscose fiber is 0.1% by weight to 1% by weight based on cellulose in the regenerated viscose fiber, and wherein the regenerated viscose fiber has a titer ranging from 0.5 to 28 dtex.

2. A process for the production of a regenerated viscose fiber according to claim 1, comprising the step of adding the hydrophobic substance to a spinning viscose or a precursor thereof.

3. A product comprising the regenerated viscose fiber according to claim 1.

4. The product according to claim 3, wherein the product is selected from the group consisting of sanitary products, medical products, papers, wet-laid nonwovens, textile products, nonwoven fabrics, and filter media.

5. The product according to claim 4, wherein the sanitary products are selected from the group consisting of cover sheets and back sheets.

6. The product according to claim 4, wherein the medical products are wound dressings.

7. The product according to claim 4, wherein the textile products are selected from the group consisting of sportswear and protective clothing.

8. The product according to claim 4, wherein the filter media are cigarette filters.

* * * * *